(12) United States Patent
Lai et al.

(10) Patent No.: US 10,292,546 B2
(45) Date of Patent: May 21, 2019

(54) URINAL CARTRIDGE AND URINAL HAVING THE SAME

(71) Applicant: Kelvin Yi-Tse Lai, Hsinchu (TW)

(72) Inventors: Kelvin Yi-Tse Lai, Hsinchu (TW); Min-Chih Hsuan, Hsinchu (TW)

(*) Notice: Subject to any disclaimer, the term of this patent is extended or adjusted under 35 U.S.C. 154(b) by 105 days.

(21) Appl. No.: 15/669,475

(22) Filed: Aug. 4, 2017

(65) Prior Publication Data

US 2018/0035851 A1 Feb. 8, 2018

(30) Foreign Application Priority Data

Aug. 8, 2016 (TW) .............................. 105211966 U

(51) Int. Cl.
*G01F 1/05* (2006.01)
*A47K 11/12* (2006.01)
*E03D 13/00* (2006.01)
*G01N 33/94* (2006.01)

(52) U.S. Cl.
CPC ............ *A47K 11/12* (2013.01); *E03D 13/007* (2013.01); *G01F 1/05* (2013.01); *G01N 33/94* (2013.01)

(58) Field of Classification Search
CPC ......... A47K 11/12; E03D 13/007; G01F 1/05; G01N 33/94; G01N 33/50

USPC .................................................. 4/144.1, 309
See application file for complete search history.

(56) References Cited

U.S. PATENT DOCUMENTS

| 6,425,411 B1 * | 7/2002 | Gorges ..................... E03C 1/281 4/144.1 |
| 10,077,546 B2 * | 9/2018 | McAlpine ............... A47K 11/12 |
| 2008/0028504 A1 * | 2/2008 | Higgins ................... E03C 1/281 4/144.1 |
| 2013/0205483 A1 * | 8/2013 | Lagobi ................... E03D 13/007 4/144.1 |

\* cited by examiner

*Primary Examiner* — Tuan N Nguyen
(74) *Attorney, Agent, or Firm* — Hamre, Schumann, Mueller & Larson, P.C.

(57) ABSTRACT

A cartridge is adapted to be inserted removably into a drain hole of a urinal, and includes a cartridge body, a guide plate member, a detecting module and a filter unit. The cartridge body has an internal space having an opening. The guide plate member is disposed in the opening, and is perforated to guide liquid which exits the urinal via the drain hole to flow therethrough into the internal space. The detecting module includes a drug-detecting chip for detecting presence of a specified drug, and a controlling chip for controlling operation of the drug-detecting chip according to measured displacement of the guide plate member. The filter unit utilizes a channel to direct the liquid from

10 Claims, 3 Drawing Sheets

URINAL CARTRIDGE AND URINAL HAVING THE SAME

CROSS-REFERENCE TO RELATED APPLICATION

This application claims priority of Taiwanese Patent Application No. 105211966, filed on Aug. 8, 2016.

FIELD

The disclosure relates to a type of toilet or urinal, more particularly a waterless urinal and a waterless urinal cartridge.

BACKGROUND

Early intervention of adolescent substance abuse has always been an imperative issue in education. In order to seek out a student under the influence of drugs, the only mean tends to be human interaction such as spot check from the police, observation from parents and teachers, or feedback from other students. Then, the student will be asked to conduct urine drug testing at a later date. However, such drug use identification may unintentionally label the student as a drug-abuser, hurting his self-esteem. With that in mind, a less explicit measure has been sought after.

On the other hand, flush urinals tend to be commonly seen in public restroom, and each of these tends to consume around 151000 Liters of water per year, equivalent to the amount used to fill two standard swimming pools. The emergence of waterless urinal system has been a breakthrough to solve the issue with water consumption, and related industrial partners have been improving the design to further satisfy user needs ever since.

Based on the above ideas, the design of the waterless urinal system could potentially incorporate the aforementioned urine drug testing to provide an implicit mean in identifying drug users.

SUMMARY

Therefore, an object of the disclosure is to provide a urinal cartridge capable of drug detection.

Another object of the disclosure is to provide a urinal having the urinal cartridge.

Accordingly, the cartridge is adapted to be inserted removably into a drain hole of a urinal, and includes a cartridge body, a guide plate member, a detecting module and a filter unit. The cartridge body has an internal space that has an opening. The guide plate member disposed in the opening of the cartridge body, and is perforated to guide liquid which exits the urinal via the drain hole to flow therethrough into the internal space. The detecting module disposed in the internal space, and includes a drug-detecting chip for detecting presence of a specified drug, and a controlling chip for controlling operation of the drug-detecting chip according to measured displacement of the guide plate member. The filter unit is disposed in the internal space, and has a channel for directing the liquid which passes the guide plate member to flow to the drug-detecting chip.

Accordingly, the urinal includes a urinal body and a cartridge. The urinal body has a drain hole. The cartridge includes a cartridge body, a guide plate, and detecting module and a filter unit. The cartridge body is inserted removably into the drain hole of the urinal body, and has an internal space having an opening. The guide plate member is disposed in the opening of the cartridge body, and is perforated to guide liquid which exits the urinal body via the drain hole to flow therethrough into the internal space. The detecting module is disposed in the internal space, and includes a drug-detecting chip for detecting presence of a specified drug, and a controlling chip for controlling operation of the drug-detecting chip according to measured displacement of the guide plate member. The filter unit is disposed in the internal space, and has a channel for directing the liquid which passes the guide plate member to flow to the drug-detecting chip.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 1:
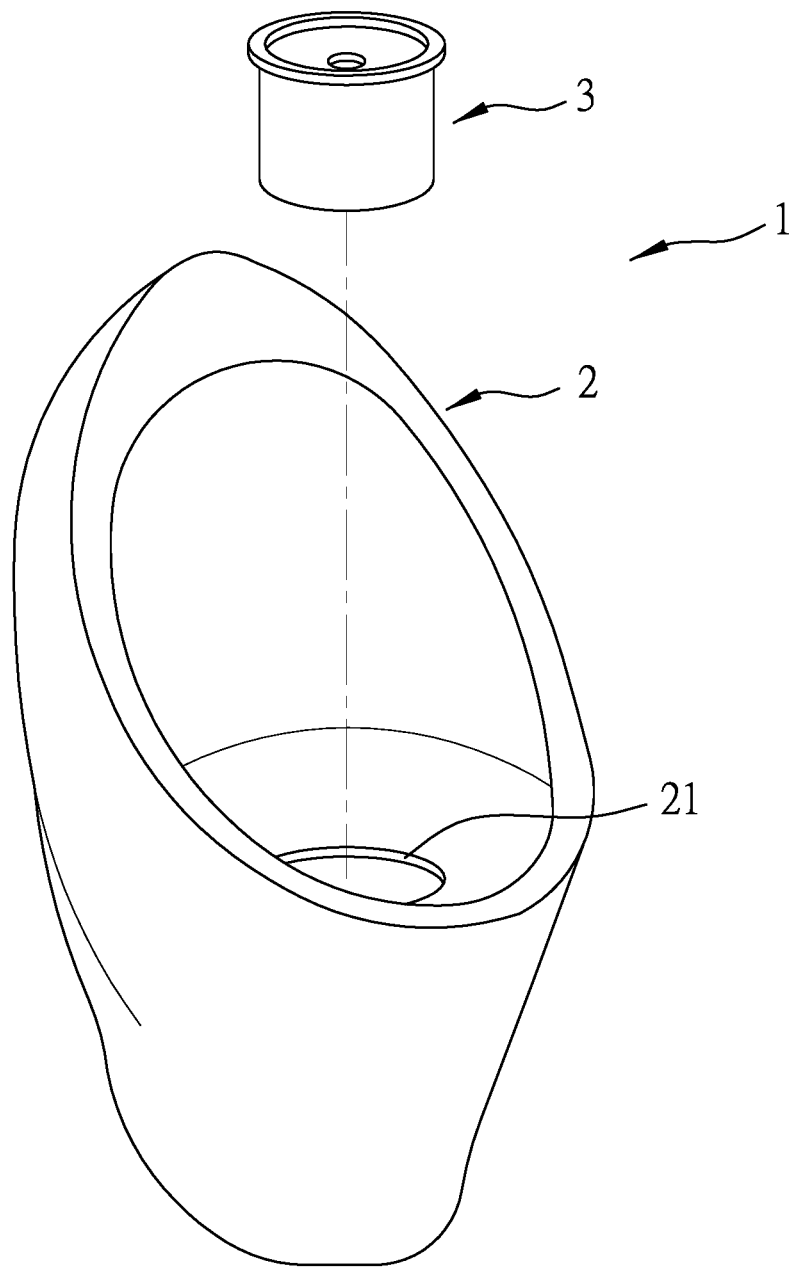
FIG. 1 is an exploded perspective view of an embodiment of a urinal cartridge according to the disclosure and a urinal body of a urinal.
Figure 2:
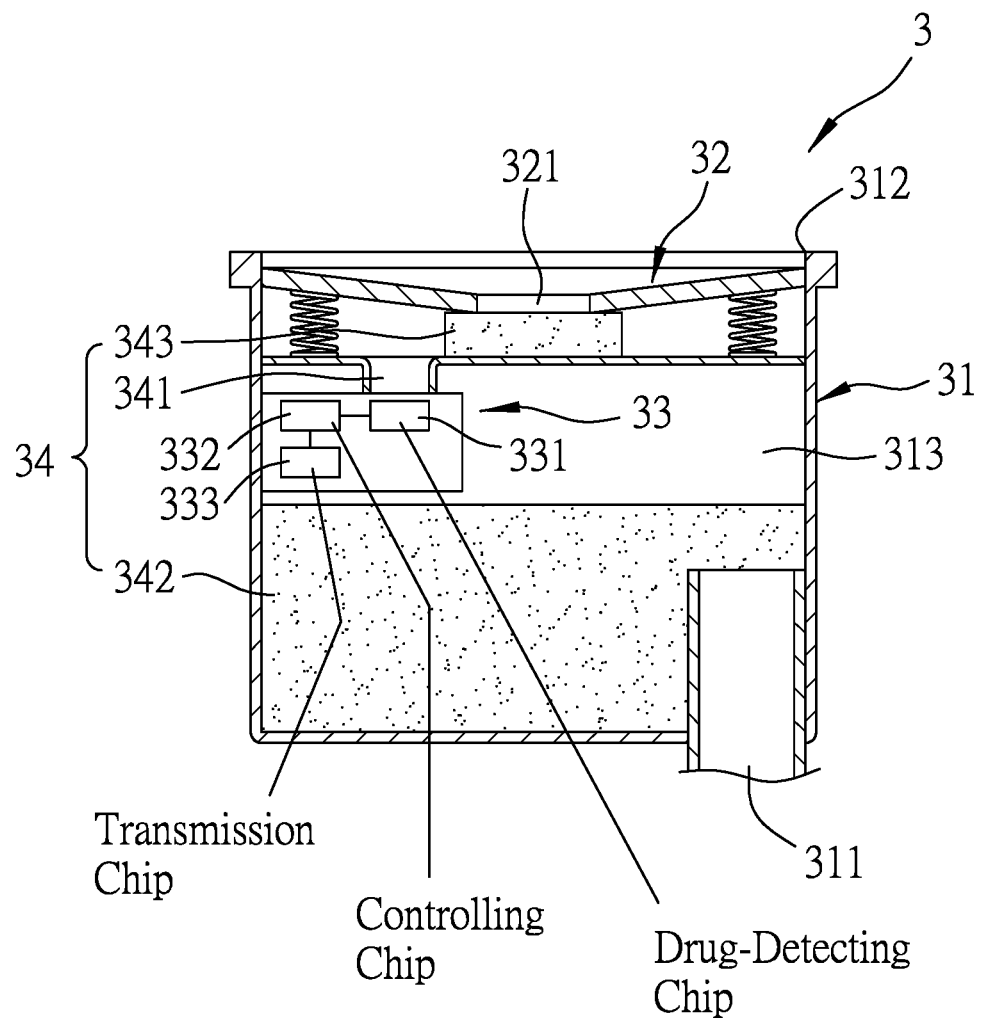
FIG. 2 is a sectional view of the embodiment.

Referring to FIGS. 1 and 2, an embodiment of a cartridge according to the disclosure is adapted to be installed removably into a urinal 1 for both sanitation and drug-detection purposes.

The urinal 1 includes a urinal body 2, and the urinal body 2 has a drain hole 21.

The cartridge 3 is adapted to be inserted removably into the drain hole 21, and includes a cartridge body 31, a guide plate member 32, a detecting module 33 and a filter unit 34.

In this embodiment, the cartridge body 31 has an internal space 313 that has an opening 312 and an outlet hole 311 communicating fluidly the internal space 313 with the external environment.

The guide plate member 32 is disposed in the opening 312 of the cartridge body 31, and is perforated to guide liquid which exits the urinal via the drain hole 21 to flow therethrough into the internal space 313. Specifically, the guide plate 32 is formed with a central hole 321 in a center thereof.

Figure 3:
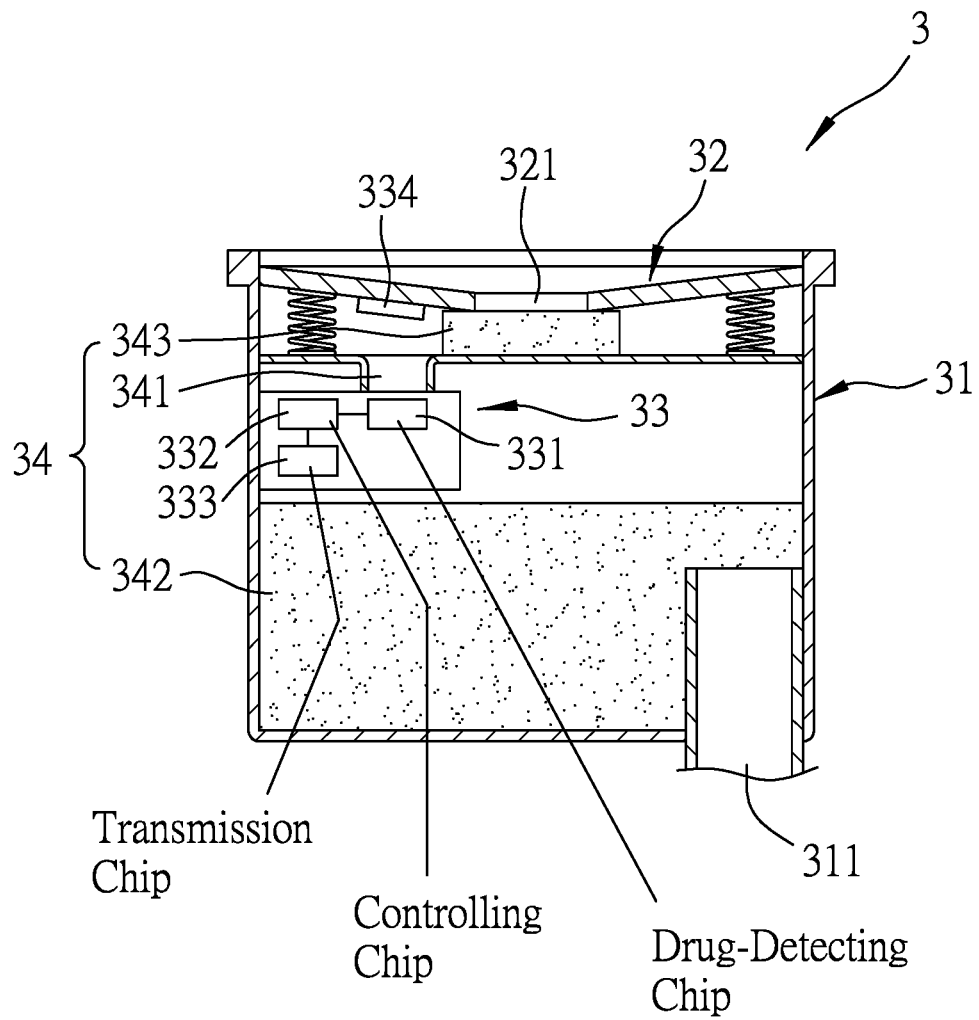
FIG. 3 is a sectional view illustrating the embodiment being mounted with an accelerometer.

The detecting module 33 is disposed in the internal space 313 and includes a drug-detecting chip 331 for detecting presence of a specified drug, a controlling chip 332 for controlling operation of the drug-detecting chip 331 according to the displacement of the guide plate member 32 which is measured by the controlling chip 332, and a transmission chip 333 for wirelessly transmitting the detected result of the drug-detecting chip 331. While the drug-detecting chip 331 is built to detect specific substances, including identified drugs, it can also be configured to measure disease index for certain disease such as diabetes and gout to assist medical institution to monitor users' health status. When the guide plate member 32 is displaced by an external force (urine), the controlling chip 332 will detect and measure the displacement of the guide plate member 32 to determine whether or not the drug-detecting chip 331 should be activated to detect specific substances. If so, the transmission chip 333 will transmit the detected outcome from the drug-detecting chip 331. Referring to FIG. 3, the detecting module 33 further includes an accelerometer 334 for measuring acceleration of the guide plate member 32, improving the displacement measurement.

The filter unit 34 is disposed in the internal space 313, and has a channel 341 for directing the liquid which passes the guide plate member 32 to flow to the drug-detecting chip 331, a degradation powder subunit 342, and an isolating film 343. The degradation powder subunit 342, filled with microorganisms that can break down the urine, is disposed in the internal space 313 and covers the outlet hole 311, such that the liquid flows through the degradation powder subunit 342 before exiting the internal space 313 via the outlet hole 311. The isolating film 343 is disposed downstream of and aligned with the central hole 321of the guide plate member 32 for preventing spreading of the odor as well as backflow of the liquid that has passed through the guide plate member 32. In this embodiment, the guide plate member 32 is mounted onto the channel 341 via an elastic element, such as spring, and is capable to be displaced against the cartridge body 31.

When a user utilize the urinal 1, the liquid expelled will be propelled into the guide plate member 32, and the isolating film 343 will prevent backflow of the liquid and spreading of the odor. The liquid initially flows into the internal space 313 and, guided by the channel 341, traverses through the drug-detecting chip 331 of the detecting module 33 and finally passes through the degradation powder subunit 342 to be broken down, later leading toward the outlet hole 311 to be released. Interestingly, when the liquid flows through the drug-detecting chip 331, the controlling chip 332 has already detected the displacement of the guide plate member 32, determining whether the drug-detecting chip 331 should begin the detection or not. Afterward, the transmission chip 333 wirelessly delivers the detected outcome to a predetermined receiving end, allowing the receiving end to be notified whether the liquid contains the substance of interest.

Given that a typical men's restroom tend to have more than one urinal, the cartridge 3 may be placed randomly into one of the urinals for random inspection, in such way that users would be unaware of its presence. In conjunction with existing security cameras, it is possible to narrow down the potential drug abusers without getting them prematurely labeled by their social circles, minimizing the psychological impact it may have brought along the inspection process.

In summary, the disclosure is to provide a cartridge 3 capable of drug detection, as well as a no flush urinal containing the cartridge 3, both of which are capable in reducing water consumption as well as detecting drugs from the user's urine, further preventing drug consumption.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A cartridge adapted to be inserted removably into a drain hole of a urinal, said cartridge comprising:
   a cartridge body having an internal space that has an opening;
   a guide plate member disposed in said opening of said cartridge body, and being perforated to guide liquid which exits the urinal via said drain hole to flow therethrough into said internal space;
   a detecting module disposed in said internal space, and including a drug-detecting chip for detecting presence of a specified drug, and a controlling chip for controlling operation of said drug-detecting chip according to measured displacement of said guide plate member; and
   a filter unit disposed in said internal space, and has a channel for directing the liquid which passes said guide plate member to flow to said drug-detecting chip.

2. The cartridge as claimed in claim 1, wherein said detecting module further includes an accelerometer for measuring acceleration of said guide plate member.

3. The cartridge as claimed in claim 1, wherein:
   said cartridge body further has at least one outlet hole communicating fluidly said internal space with the external environment; and
   said filter unit further has a degradation powder subunit disposed in said internal space and covering said at least one outlet hole such that the liquid flows through said degradation powder subunit before exiting said internal space via said at least one outlet hole.

4. The cartridge as claimed in claim 1, wherein:
   said guide plate member is formed with a central hole in a center thereof; and
   said filter unit further has an isolating film disposed downstream of and aligned with said central hole for preventing backflow of the liquid which has passed through said guide plate member.

5. The cartridge as claimed in claim 1, wherein said detecting module further includes a transmission chip for wirelessly transmitting the detected result of said drug-detecting chip.

6. A urinal comprising:
   a urinal body having a drain hole; and
   a cartridge including
      a cartridge body that is inserted removably into said drain hole of said urinal body, and that has an internal space having an opening,
      a guide plate that is disposed in said opening of said cartridge body, and that is perforated to guide liquid which exits said urinal body via said drain hole to flow therethrough into said internal space,
      a detecting module that is disposed in said internal space, and that includes a drug-detecting chip for detecting presence of a specified drug, and a controlling chip for controlling operation of said drug-detecting chip according to measured displacement of said guide plate member, and
      a filter unit that is disposed in said internal space, and that has a channel for directing the liquid which passes said guide plate member to flow to said drug-detecting chip.

7. The urinal as claimed in claim 6, wherein said detecting module further includes an accelerometer for measuring acceleration of said guide plate member.

8. The urinal as claimed in claim 6, wherein:
said cartridge body further has at least one outlet hole communicating fluidly said internal space with the external environment; and
said filter unit further has a degradation powder subunit disposed in said internal space and covering said at least one outlet hole such that the liquid flows through said degradation powder subunit before exiting said internal space via said at least one outlet hole.

9. The urinal as claimed in claim 6, wherein:
said guide plate member is formed with a central hole in a center thereof; and
said filter unit further has an isolating film disposed downstream of and being aligned with said central hole for preventing backflow of the liquid which passes said guide plate member.

10. The urinal as claimed in claim 6, wherein said detecting module further includes a transmission chip for wirelessly transmitting the detected result of said drug-detecting chip.

* * * * *